US009827003B2

(12) United States Patent
Ilizaliturri-Sanchez et al.

(10) Patent No.: US 9,827,003 B2
(45) Date of Patent: Nov. 28, 2017

(54) ARTHROSCOPIC RESECTION DEVICE

(75) Inventors: Victor Ilizaliturri-Sanchez, Col Arenal de Guadalupe (MX); Dean Matsuda, Los Angeles, CA (US); Mathew Erle Mitchell, Pelham, NH (US); Rafal Z Jezierski, Middleton, MA (US); Bryan S Jones, West Roxbury, MA (US)

(73) Assignee: Smith & Nephew, Inc., Memphis, TN (US)

(*) Notice: Subject to any disclaimer, the term of this patent is extended or adjusted under 35 U.S.C. 154(b) by 260 days.

(21) Appl. No.: 13/397,000

(22) Filed: Feb. 15, 2012

(65) Prior Publication Data
US 2013/0072935 A1    Mar. 21, 2013

Related U.S. Application Data

(60) Provisional application No. 61/442,961, filed on Feb. 15, 2011, provisional application No. 61/545,345, filed on Oct. 10, 2011, provisional application No. 61/567,577, filed on Dec. 6, 2011.

(51) Int. Cl.
    *A61B 17/32*  (2006.01)
    *A61B 17/00*  (2006.01)
    *A61B 90/00*  (2016.01)

(52) U.S. Cl.
    CPC ........... *A61B 17/320016* (2013.01); *A61B 17/32002* (2013.01); *A61B 2017/00407* (2013.01); *A61B 2017/00991* (2013.01); *A61B 2090/08021* (2016.02)

(58) Field of Classification Search
    CPC .................. A61B 17/320016; A61B 17/32002

USPC ............................ 606/79–80, 170–171, 83
See application file for complete search history.

(56) References Cited

U.S. PATENT DOCUMENTS

| | | | |
|---|---|---|---|
| 4,723,545 A | | 2/1988 | Nixon et al. |
| 2003/0055404 A1* | | 3/2003 | Moutafis ................. 604/540 |
| 2003/0083681 A1 | | 5/2003 | Moutafis et al. |
| 2003/0083684 A1* | | 5/2003 | Cesarini et al. ............ 606/170 |
| 2003/0191487 A1 | | 10/2003 | Robison et al. |
| 2003/0195539 A1 | | 10/2003 | Attinger et al. |
| 2005/0054972 A1* | | 3/2005 | Adams et al. .................. 604/22 |
| 2006/0155210 A1* | | 7/2006 | Beckman .......... A61B 10/0275 600/567 |
| 2007/0027447 A1* | | 2/2007 | Theroux et al. .............. 606/41 |

(Continued)

FOREIGN PATENT DOCUMENTS

| EP | 1 676 537 A1 | 7/2006 |
|---|---|---|
| EP | 1676537 | 7/2006 |

(Continued)

OTHER PUBLICATIONS

Office action received in corresponding European application No. 12713403.9 dated May 22, 2014.

(Continued)

*Primary Examiner* — Matthew Lawson

(57) ABSTRACT

An arthroscopic resection device is disclosed. The device includes an outer member including a hub, an inner member including a hub, the inner member housed within the outer member, a tube coupled to the outer member, and means for allowing longitudinal movement of the outer member relative to the inner member, the means coupled to the tube. A method of tissue repair and other arthroscopic resection devices are also disclosed.

24 Claims, 23 Drawing Sheets

(56) References Cited

U.S. PATENT DOCUMENTS

| | | | | |
|---|---|---|---|---|
| 2010/0094298 A1* | 4/2010 | Alleyne | ............................ | 606/80 |
| 2011/0184420 A1* | 7/2011 | Barnhouse et al. | ............ | 606/84 |
| 2012/0209274 A1* | 8/2012 | Belaney et al. | ................ | 606/84 |

FOREIGN PATENT DOCUMENTS

| | | |
|---|---|---|
| EP | 1 938 757 A1 | 7/2008 |
| EP | 1938757 | 7/2008 |
| EP | 2218411 | 8/2010 |
| JP | H11-188043 | 7/1999 |
| JP | 2006-187617 | 7/2006 |
| JP | 2006-192267 | 7/2006 |
| JP | 2006187617 | 7/2006 |
| JP | 2009-268632 | 11/2009 |
| SU | 596229 | 3/1978 |
| WO | 9620749 | 7/1996 |

OTHER PUBLICATIONS

International Preliminary Report on Patentability received in corresponding International Application No. PCT/US2012/025190, dated Aug. 29, 2013.

International Search Report and Written Opinion regarding international patent No. PCT/US2012/025190 dated Jun. 18, 2012.

CN OA for CN201280009122.6 dated Aug. 24, 2015, 10 pages.

Office Action for MX app No. MX/a/2013/009428 dated Jul. 21, 2015, 4 pages.

Patent Exam Report for AU App No. 2012217764 dated Aug. 26, 2015, 3 pages.

Mexico Patent Application No. MX/a/2013/009428, communication of the substantive examination report, dated Feb. 19, 2016 (Translation).

Australian Patent Application No. 2012217764, Patent Examination Report No. 2, dated Mar. 22, 2016.

Russian Application No. 2013141663/14(063734), Office Action dated Nov. 25, 2015 (Translation).

Japanese Office Action (Translation), Application No. 2013-554565, dated Dec. 14, 2015.

Office Action in Mexican Patent Application No. MX/a/2013/009428, dated Jul. 13, 2016.

Office Action in European Patent Application No. 12713403.9-1654, dated Nov. 10, 2016.

Third Office Action in Chinese Patent Application No. 201280009122.6, dated Nov. 29, 2016.

Chinese Patent Application No. 201280009122.6 Second Office Action (English Translation) dated May 11, 2016.

Final Office Action in Japanese Patent Application No. 2013-554565, dated Jul. 11, 2016.

Office action in Japanese patent application No. 2013554565 dated Jun. 12, 2017, 3 pages.

Office Action in Chinese Patent Application No. 201280009122.6 dated Apr. 12, 2017; 4 pages.

Office action (translation) in Japanese Patent Application No. 2013-555465, dated Jan. 4, 2017.

\* cited by examiner

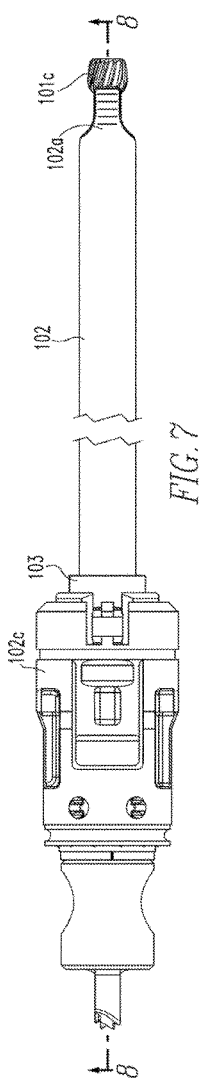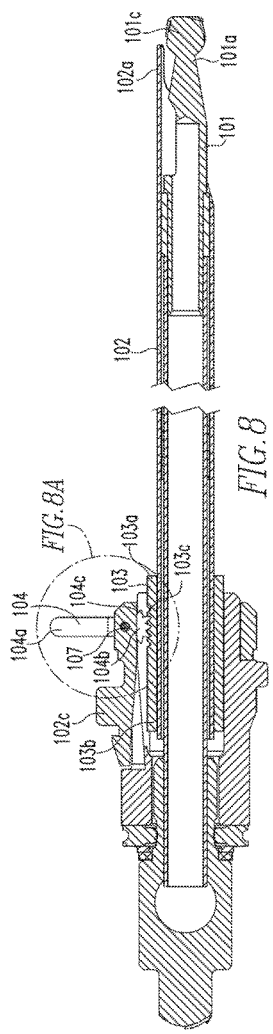

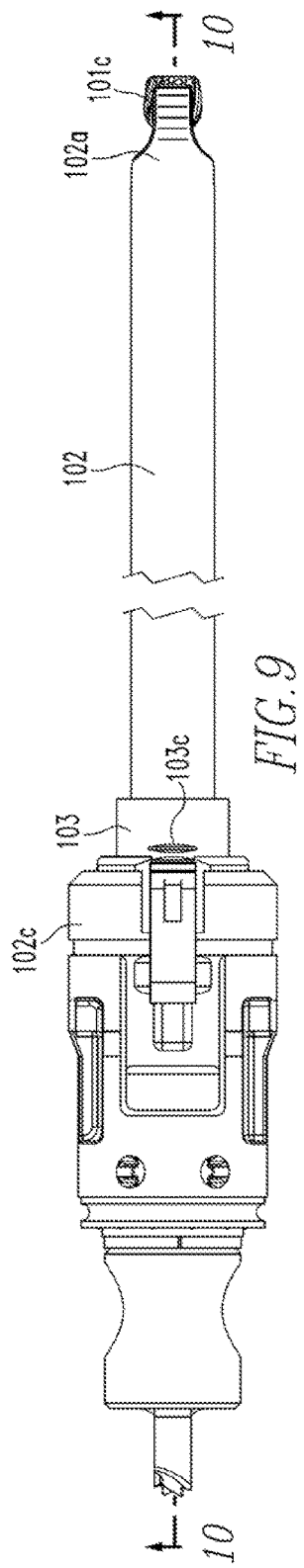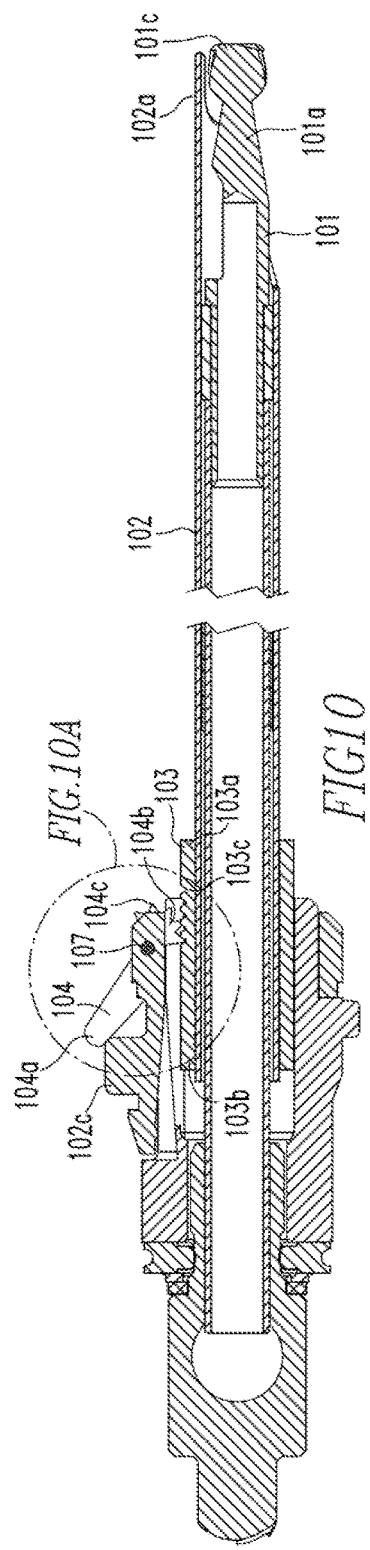

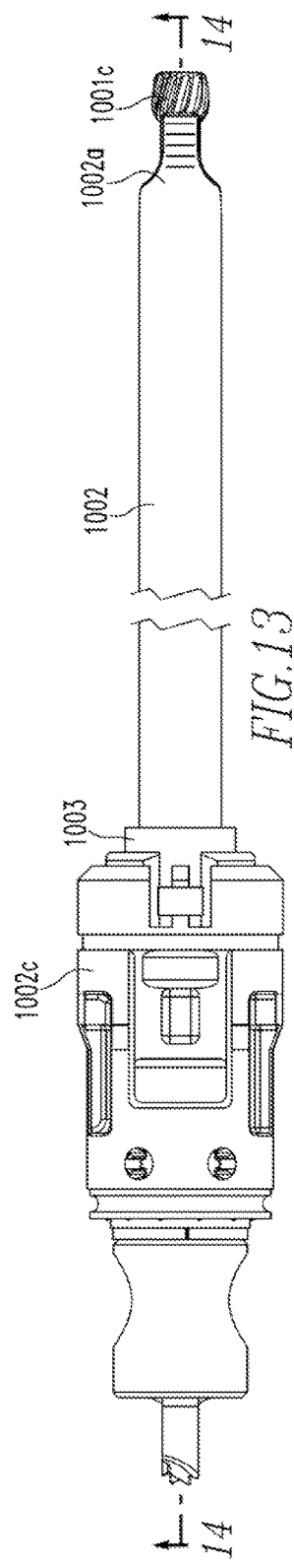
FIG.13
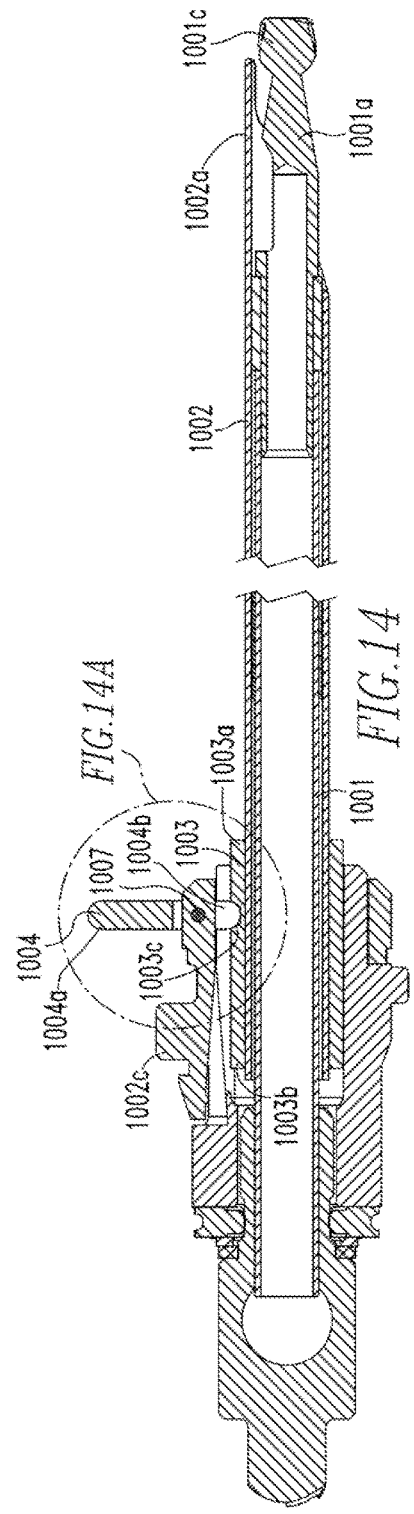
FIG.14A
FIG.14

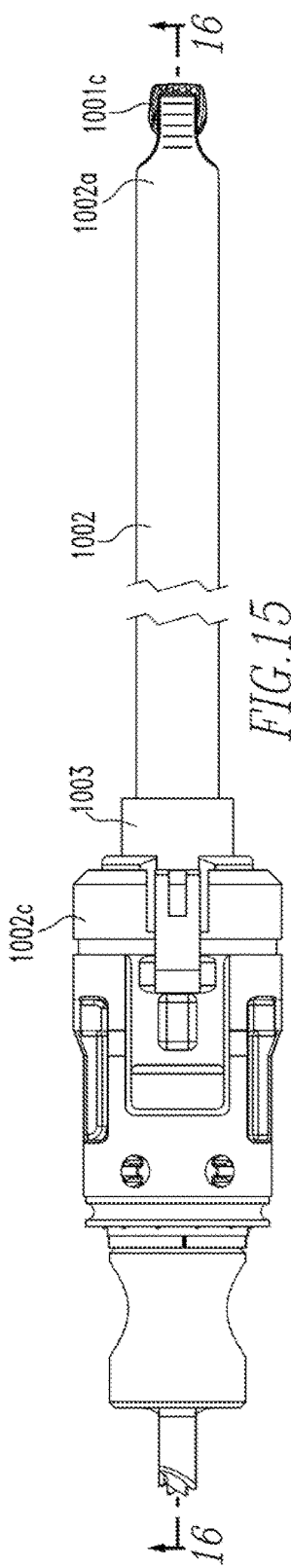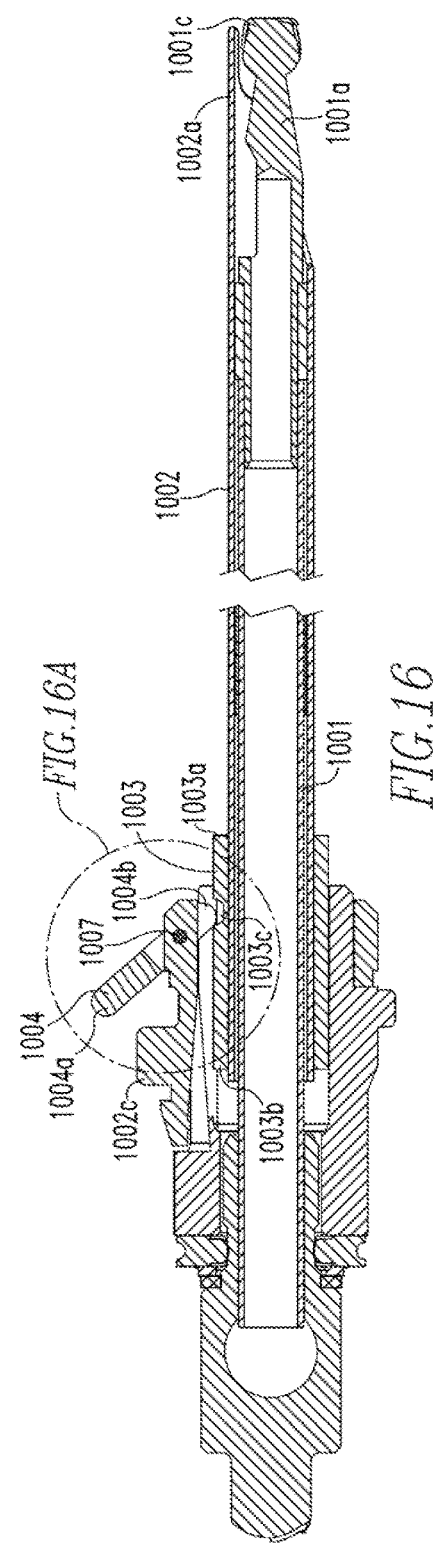

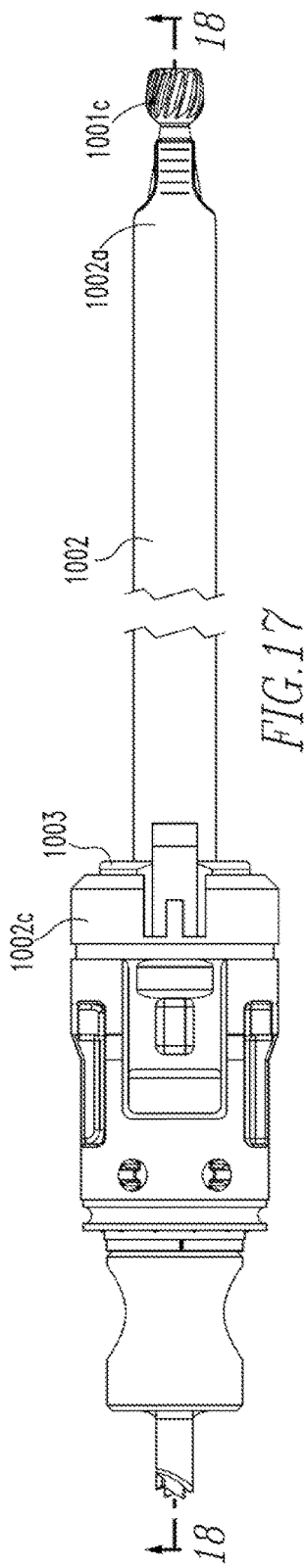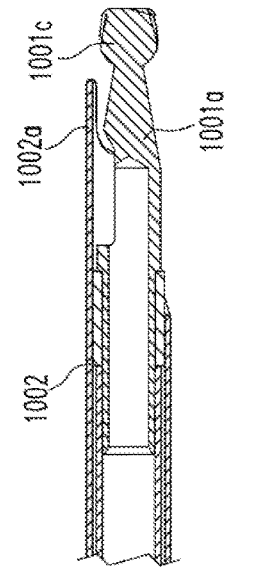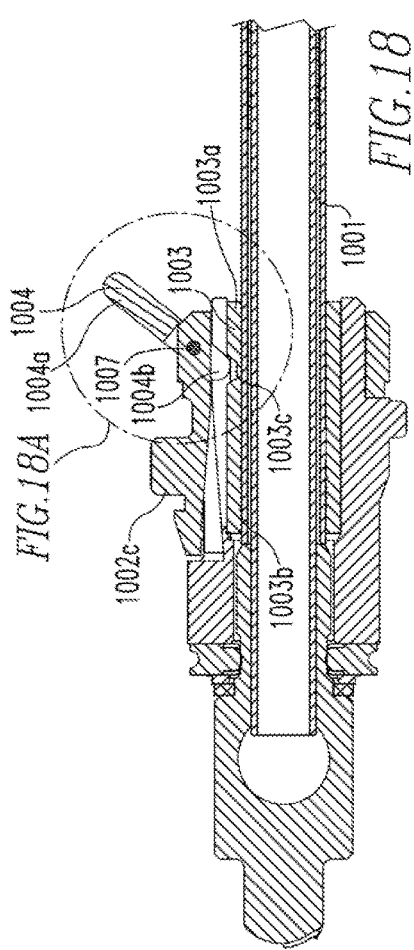

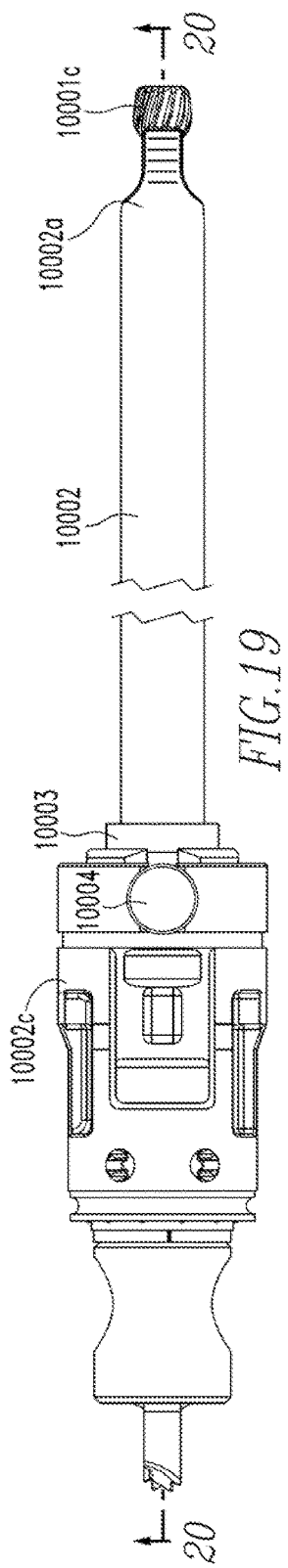
FIG. 19
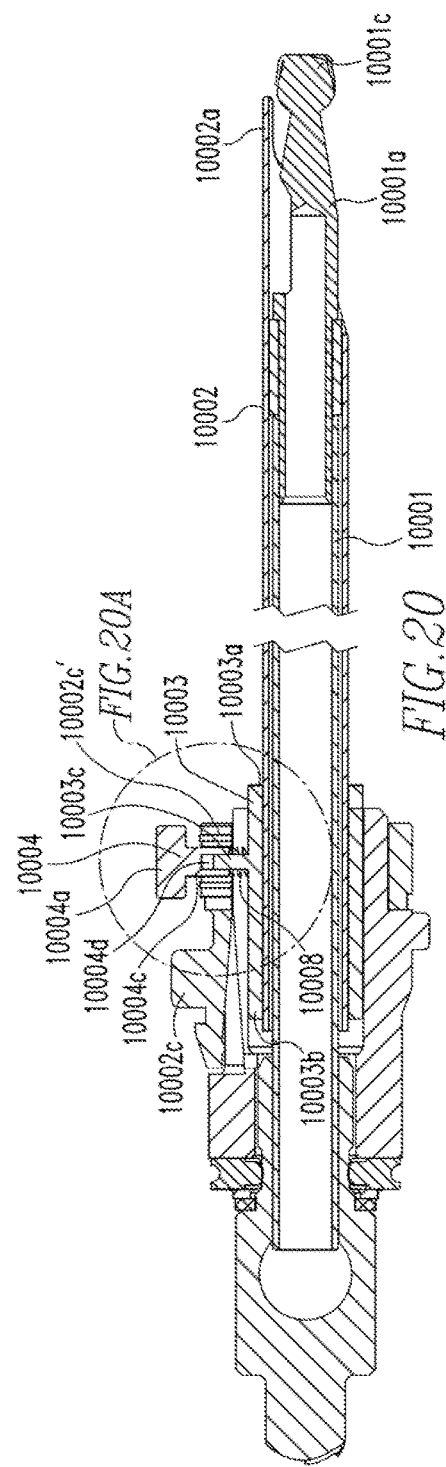
FIG. 20A
FIG. 20

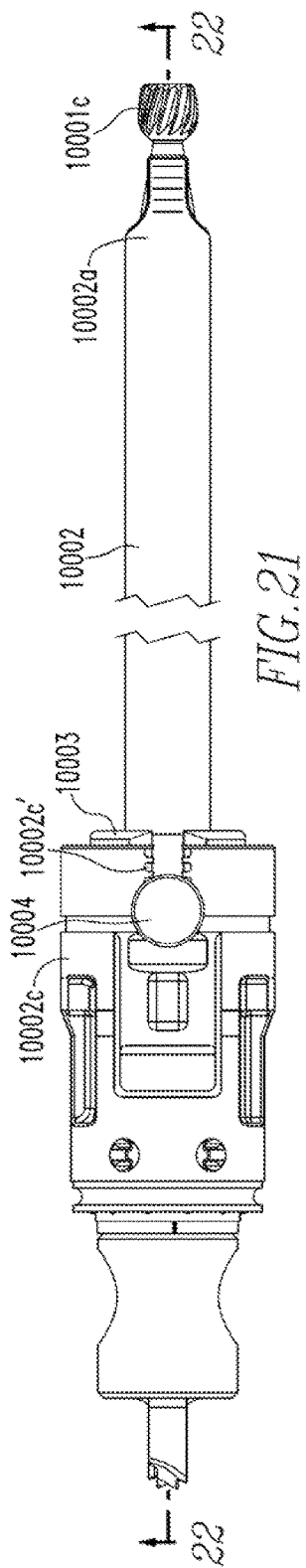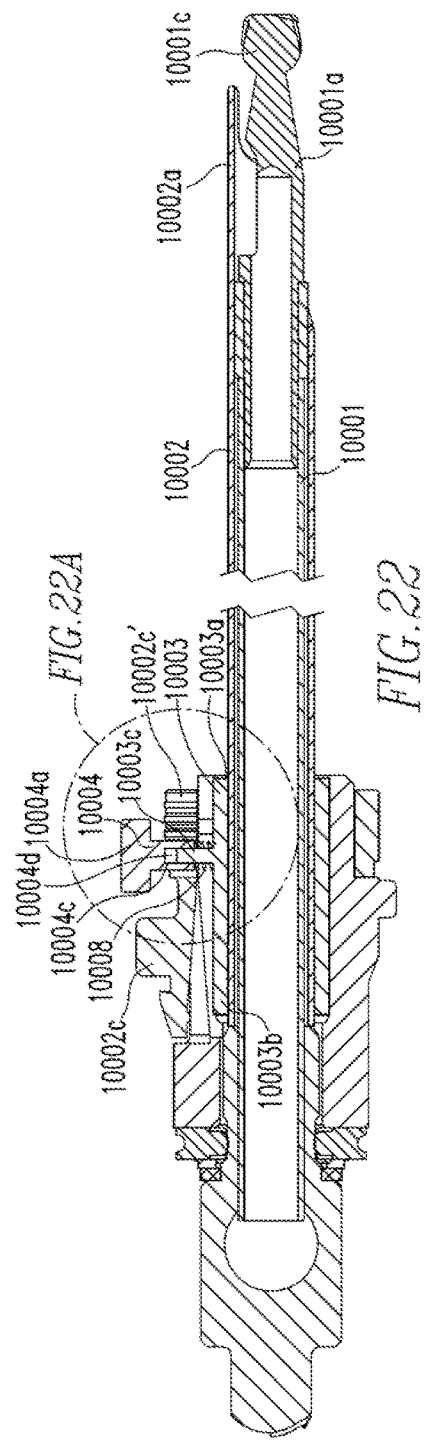

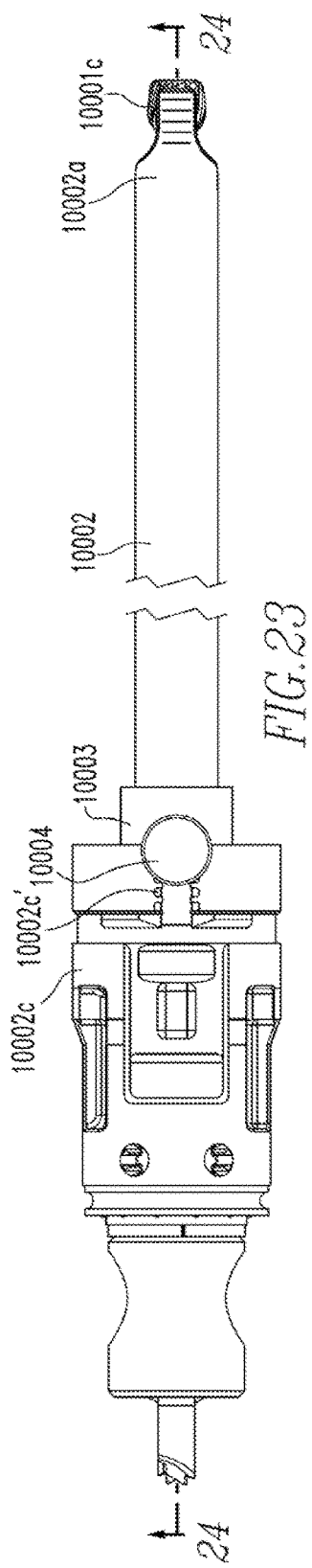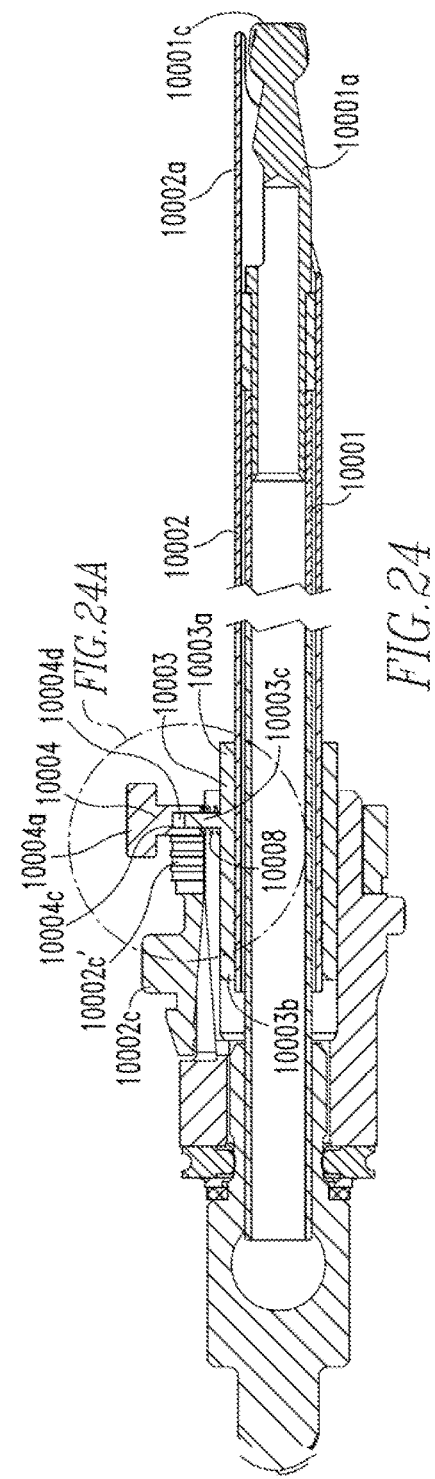

# ARTHROSCOPIC RESECTION DEVICE

CROSS-REFERENCE TO RELATED APPLICATIONS

This application claims priority to U.S. Patent Application No. 61/442,961, filed on Feb. 15, 2011, U.S. Patent Application No. 61/545,345, filed on Oct. 10, 2011, and U.S. Patent Application No. 61/567,577, filed on Dec. 6, 2011, the disclosures of which are incorporated herein in their entireties.

BACKGROUND

Field of Technology

The present disclosure relates to arthroscopic resection devices in general and, specifically, to an arthroscopic resection device having an adjustable outer member.

Related Art

Arthroscopic resection devices spin about their axes at high rates. So that tissue surrounding a surgical area does not become inadvertently resected, some of these devices have an outer member that partially covers the working end. The drawback to this is that the outer member can occasionally get in the way of a surgeon's line of site potentially changing the surgeon's perception of how much tissue is being removed. Currently, the options for dealing with this include the use of a shorter length outer member, the use of several devices during the surgical procedure, or the use of a device that can be used with interchangeable outer members of different lengths. The drawbacks to this are limited resection capability due to the concern of inadvertently resecting surrounding tissue, increased costs due to having to open multiple resection devices per case, and the potential for damaging the cutting surface of the working end when replacing the outer members.

Therefore, a resection device that allows for a change in the location of the outer member relative to the inner member in an easier, less costly manner during surgery is needed.

SUMMARY

In an aspect, the present disclosure relates to an arthroscopic resection device. The device includes an outer member including a hub, an inner member including a hub, the inner member housed within the outer member, a tube coupled to the outer member, and means for allowing longitudinal movement of the outer member relative to the inner member, the means coupled to the tube.

In an embodiment, a distal end of the tube includes threads and a proximal end of the tube includes a slot. In another embodiment, a pin is coupled to the outer member, the pin housed within the slot. In yet another embodiment, the proximal end of the tube is partially housed within the hub of the outer member. In a further embodiment, the inner member includes a burr. In yet a further embodiment, the outer member is movable along a length of the device. In an embodiment, the burr includes a flat end. In another embodiment, the outer member includes detents.

In another aspect, the present disclosure relates to a method of tissue repair. The method includes providing an arthroscopic resection device including an outer member including a hub, an inner member including a burr and a hub, the inner member housed within the outer member, a tube coupled to the outer member, and means for allowing longitudinal movement of the outer member coupled to the tube; actuating the means to move the outer member relative to the inner member, and operating the device to repair tissue.

In an embodiment, moving the outer member relative to the inner member allows for a portion of the burr to be covered by the outer member or none of the burr to be covered by the outer member. In another embodiment, a distal end of the tube includes the threads and a proximal end of the tube includes a slot. In yet another embodiment, a pin is coupled to the outer member, the pin housed within the slot. In a further embodiment, the proximal end of the tube is partially housed within the hub of the outer member. In yet a further embodiment, the outer member is movable along a length of the device. In an embodiment, the burr includes a flat end. In another, embodiment, the tissue is an acetabulum. In another embodiment, the outer member includes detents. In yet another embodiment, the means includes threads in engagement with threads of the tube.

In an embodiment, the means includes a lever. In another embodiment, the means includes a slidable button. In yet another embodiment, the means includes a ratchet.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 7 shows a top view of an alternative embodiment of the arthroscopic resection device of the present disclosure with the ratchet in a non-activated position.

FIG. 8 shows a cross-sectional side view of the arthroscopic resection device of FIG. 7.

FIG. 9 shows another top view of the alternative embodiment of the arthroscopic resection device of FIG. 7 with the ratchet in an activated position.

FIG. 10 shows a cross-sectional side view of the arthroscopic resection device of FIG. 9.

FIG. 13 shows a top view of another alternative embodiment of the arthroscopic resection device of the present disclosure with the lever in a non-activated position.

FIG. 14 shows a cross-sectional side view of the arthroscopic resection device of FIG. 13.

FIG. 15 shows another top view of the alternative embodiment of the arthroscopic resection device of FIG. 13 with the lever in an activated position.

FIG. 16 shows a cross-sectional side view of the arthroscopic resection device of FIG. 15.

FIG. 17 shows yet another top view of the alternative embodiment of the arthroscopic resection device of FIG. 13 with the ratchet in an activated position.

FIG. 18 shows a cross-sectional side view of the arthroscopic resection device of FIG. 17.

FIG. 19 shows a top view of yet another alternative embodiment of the arthroscopic resection device of the present disclosure with the slidable button in a non-activated position.

FIG. 20 shows a cross-sectional side view of the arthroscopic resection device of FIG. 19.

FIG. 21 shows another top view of the alternative embodiment of the arthroscopic resection device of FIG. 19 with the slidable button in an activated position.

FIG. 22 shows a cross-sectional side view of the arthroscopic resection device of FIG. 21.

FIG. 23 shows yet another top view of the alternative embodiment of the arthroscopic resection device of FIG. 19 with the ratchet in an activated position.

FIG. 24 shows a cross-sectional side view of the arthroscopic resection device of FIG. 23.

DETAILED DESCRIPTION OF THE EMBODIMENTS

Figure 1:
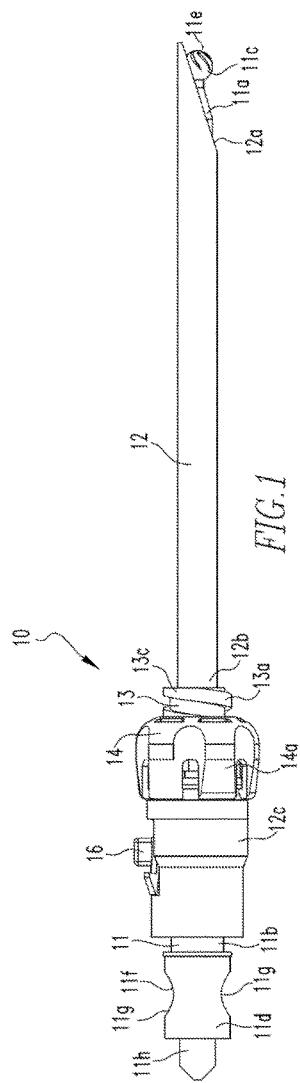
FIG. 1 shows a side view of the arthroscopic resection device of the present disclosure.

The following description of the preferred embodiment(s) is merely exemplary in nature and is in no way intended to limit the disclosure, its application, or uses.

FIGS. 1-4 show the arthroscopic resection device 10 of the present disclosure and components thereof. The device 10 includes an inner member 11, an outer member 12, a tube 13, and a means 14 for allowing longitudinal movement of the outer member 12 relative to the inner member 11. For the purposes of FIGS. 1-4, the means is a knob. The inner member 11 is in a tubular form and includes a distal end 11a and a proximal end 11b. Coupled to the distal end 11a is a burr 11c and coupled to the proximal end 11b is a hub 11d. The burr 11c includes flutes 11e, which are used to cut tissue. The distal end 11a also includes an opening (not shown) through which cut tissue enters during surgery, as will be further described below. The hub 11d of the proximal end 11b includes a through hole 11f having two openings 11g and a drive tang 11h, which, during use, is coupled to a drive shaft of a motor drive unit. The motor drive unit also includes a vacuum source, which draws cut tissue through the inner member 11, through the hole 11f and openings 11g, and out of the device 10. The inner member 11, its components, and its method of use with a motor drive unit during surgery are further described in U.S. Pat. No. 5,871,493, the disclosure of which is incorporated herein by reference in its entirety.

The outer member 12 includes an open distal end 12a and a proximal end 12b. Coupled to the proximal end 12b is a hub 12c. The hub 12c includes a hole 12d on each side of the hub 12c. As shown in FIG. 2, a pin 15 is housed within the holes 12d and the outer member 12. The hub 12c includes a latching mechanism 16 coupled to the hub 12c. As shown in FIGS. 1-4, the inner member 11 is disposed within the outer member 12. The latching mechanism 16 couples the hub 12c, and therefore the device 10, to the motor drive unit when the device 10 is placed within the motor drive unit. The latching mechanism 16 and its method of use with a motor drive unit are further described in the '493 patent.

The tube 13 includes a distal end 13a and a proximal end 13b. The distal end 13a includes threads 13c and the proximal end 13b includes a slot 13d on each side of the tube 13. The tube 13 is disposed over the outer member 12 and at least a portion of the proximal end 13b is housed within the hub 12c such that at least portions of the pin 15 are housed within the slots 13d.

The knob 14 includes fingers 14a and an internal thread (not shown). The knob 14 is disposed on the outer member 12 such that the fingers 14a are coupled to the latching mechanism 16 and the internal threads engage with the threads 13c of the tube 13. Due to engagement of the internal threads with threads 13c and the coupling of the tube 13 and the outer member 12, rotation of the knob 14 allows for movement of the tube 13 along a longitudinal axis of the device 10, and therefore the outer member 12, proximally towards the knob 14. Movement of the outer member 12 continues until portions 13d' of the slots 13d come into contact with the pin 15.

Figure 2:
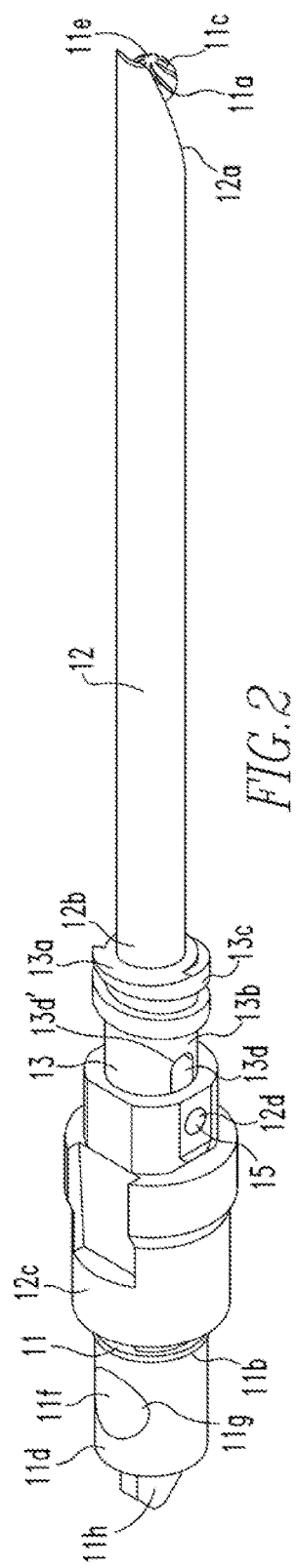
FIG. 2 shows a side view of the arthroscopic resection device of FIG. 1 without the knob or the latch.
Figure 3:
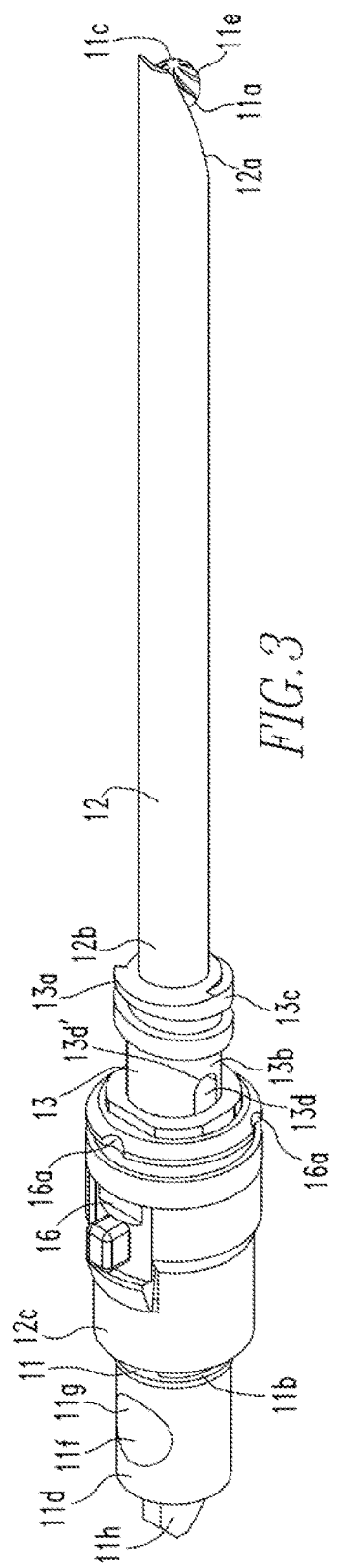
FIG. 3 shows side view of the arthroscopic resection device of FIG. 1 without the knob.
Figure 4:
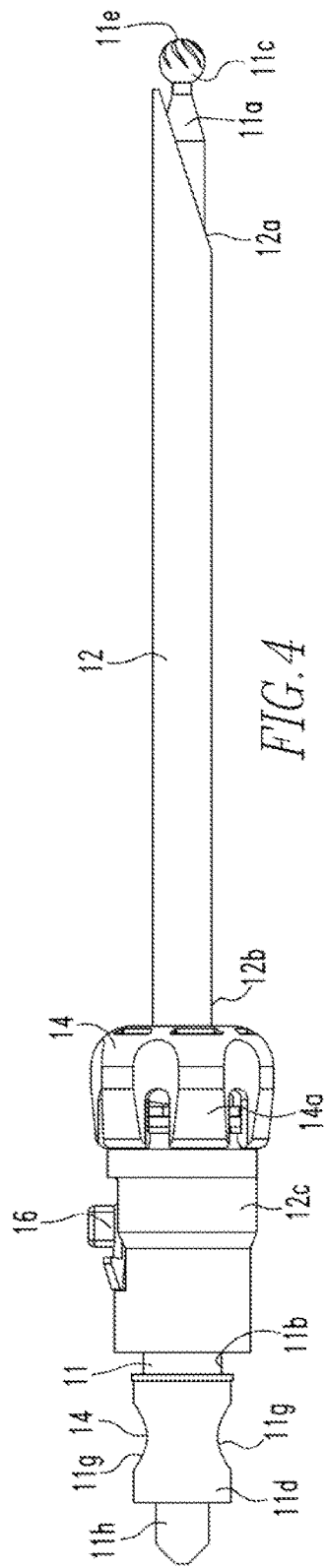
FIG. 4 shows a side view of the arthroscopic resection device of FIG. 1 with none of the burr covered.

FIG. 1 shows the location of the distal end 12a of the outer member 12 prior to axial movement of the outer member 12 proximally towards the knob 14. As is shown in FIG. 1, at least a portion of the burr 11c is covered by the outer member 12. FIG. 4 shows the location of the distal end 12a of the outer member 12 after full proximal axial movement of the outer member 12 has occurred. Full proximal axial movement of the outer member 12 refers to when portions 13d' of the slots 13d come into contact with the pin 15 and no further axial movement of the tube 13, and therefore axial movement of the outer member 12, can occur proximally towards the knob 14. As shown in FIG. 4, none of the burr 11e is covered by the outer member 12 after full axial movement of the outer member 12 has occurred. Rotation of the knob 14 in the opposite direction causes the tube 13 and the outer member 12 to move distally back towards the burr 11c until the distal end 12a of the outer member 12 has returned to the location desired by the surgeon, such as the location of the outer member 12 shown in FIG. 1.

The latching mechanism 16 includes detents 16a. At least one of the fingers 14a includes a tab (not shown) that fits within the detents 16a. The detents 16a can be used to define discrete positions or locations for the outer member 12. For example, no proximal axial movement of the outer member 12, partial proximal axial movement of the outer member 12, and full proximal axial movement of the outer member 12.

Prior to a tissue repair procedure, the user, such as a surgeon, may set the distal end 12a of the outer member 12 at the desired location. The surgeon then places the device 10 within the surgical area and operates the device 10 to repair tissue. During the procedure, the surgeon may change the location of the distal end 12a of the outer member 12 according to their liking. For example, the surgeon may position the distal end 12a of the outer member 12 around the distal end 11a of the inner member 11 and the burr lie when protection of tissue surrounding the surgical area is desired. When protection of surrounding tissue is no longer a necessity, the surgeon may retract the outer member 12 axially to move the distal end 12a of the outer member 12 away from the burr 11c. No longer will the use of several devices during the surgical procedure or a device that can be used with interchangeable outer members of different lengths, as discussed above, be needed.

Figure 5:
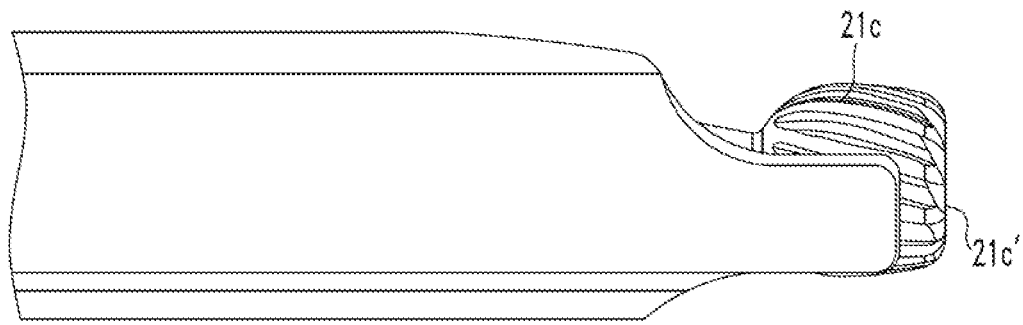
FIG. 5 shows a side view of the arthroscopic resection device of FIG. 1 having a flat burr.
Figure 6:
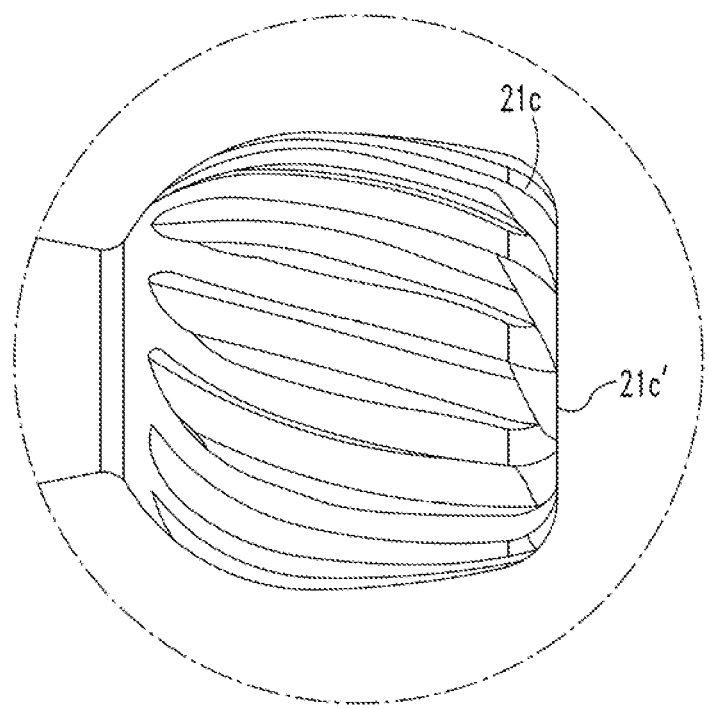
FIG. 6 shows an enlarged view of the flat burr of FIG. 5.

FIGS. 5 and 6 show a burr 21c having a flat end 21c'. Unlike the burr 11e shown in FIGS. 1-4, burr 21c has a flat end, whereas burr 11e has a rounded end. Burr 21c is useful in surgical procedures, such as acetabuloplastics, otherwise known as rim trim procedures, whereby a flat surface is created on the rim of the acetabulum with one pass of the burr 21c, rather than multiple passes with a round end burr, such as burr 11c. Burr 11c tends to leave a "valley" that has to have its edges removed in a perpendicular plane. The use of burr 21c would prevent the creation of these valleys and therefore the additional edge removal procedure.

Figure 8A:
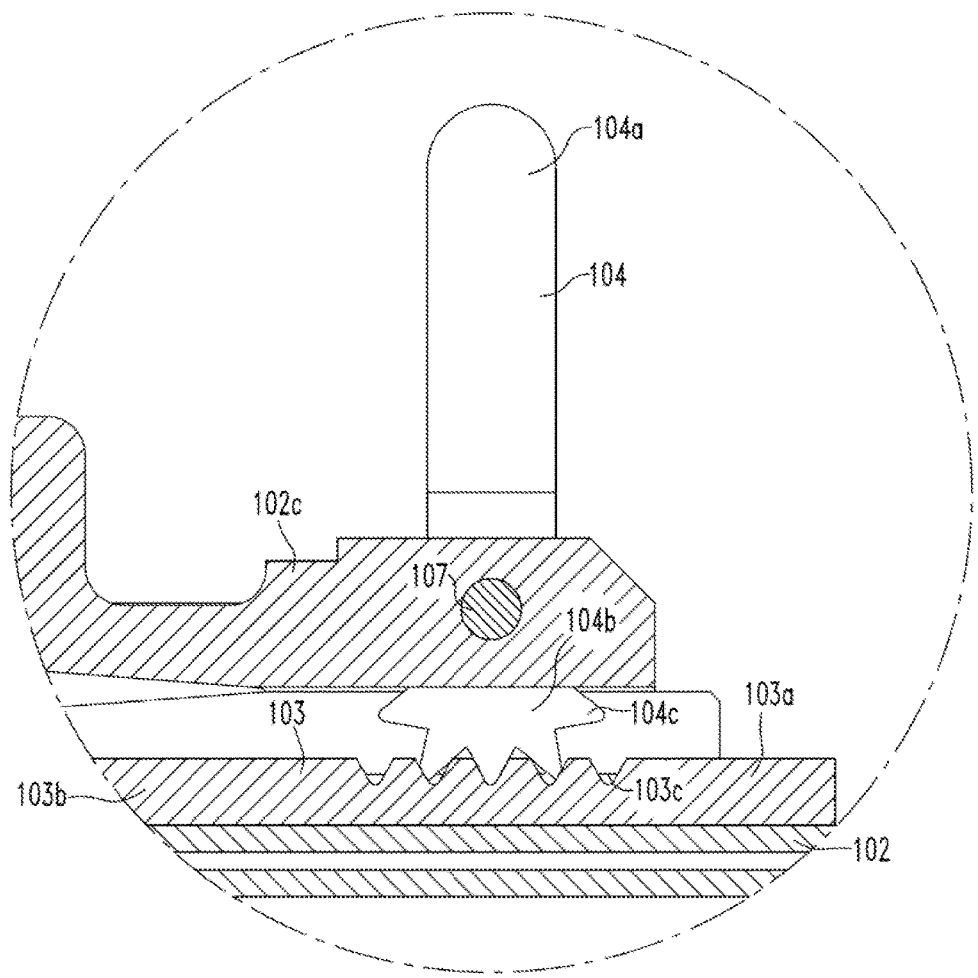
FIG. 8A is an enlarged view of the ratchet as shown in FIG. 8.
Figure 10A:
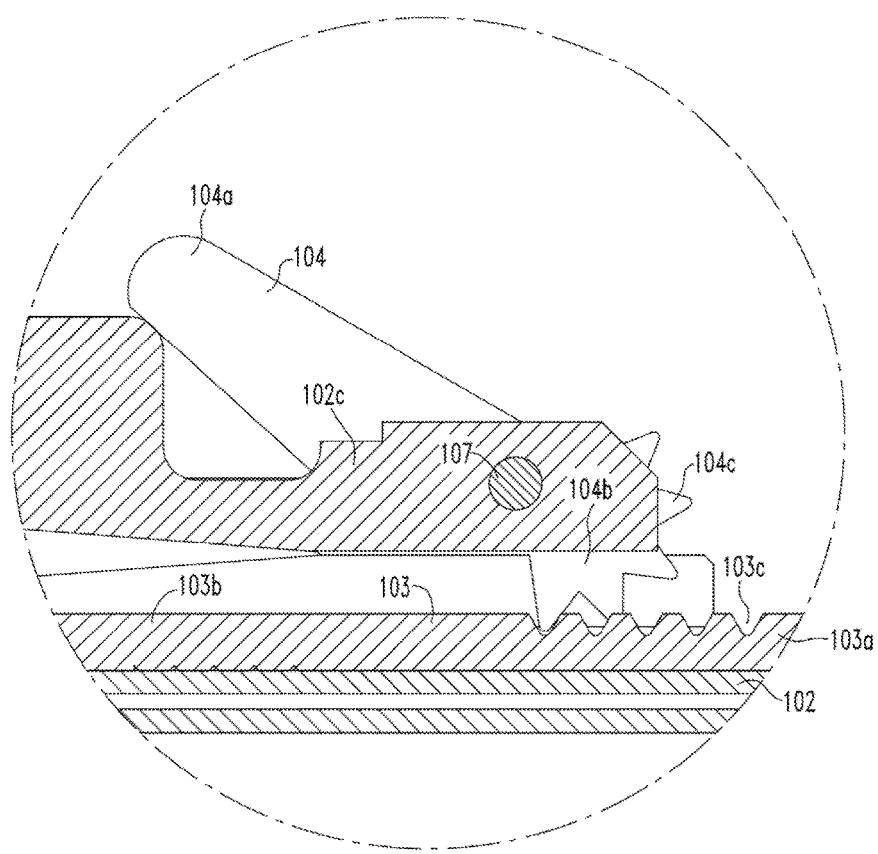
FIG. 10A shows an enlarged view of the ratchet as shown in FIG. 10.
Figure 11:
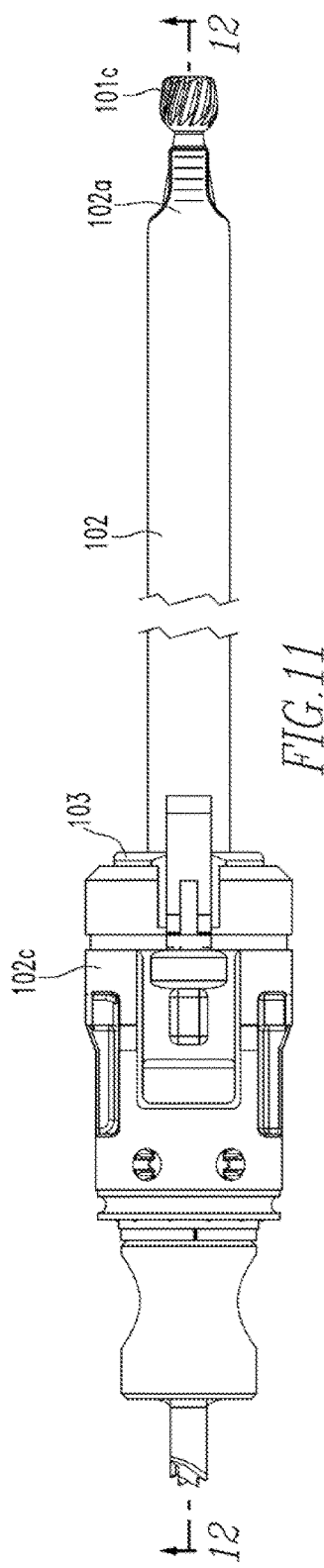
FIG. 11 shows yet another top view of the alternative embodiment of the arthroscopic resection device of FIG. 7 with the ratchet in an activated position.
Figure 12:
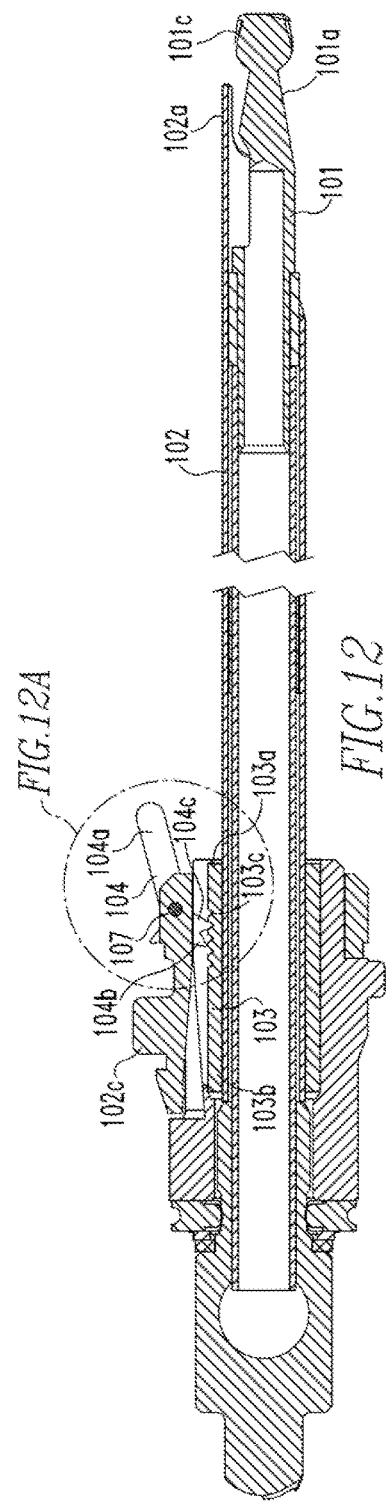
FIG. 12 shows a cross-sectional side view of the arthroscopic resection device of FIG. 11.`
Figure 12A:
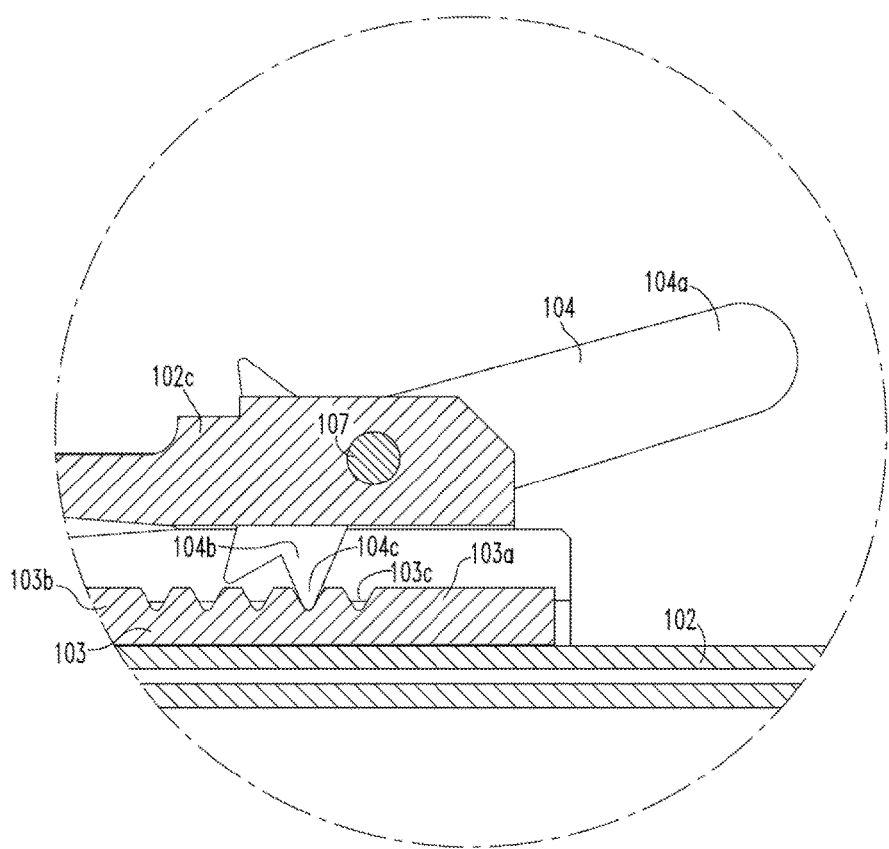
FIG. 12A shows an enlarged view of the ratchet as shown in FIG. 12.

Rather than using a tube and knob to allow for longitudinal movement of the outer member, other components may be used. FIGS. 7-12A show the use of a ratchet 104 with a tube 103. Similar to tube 13, tube 103 includes a distal end 103a and a proximal end 103b. The distal end 103a includes teeth 103c extending along at least a portion of the distal end 103a. The ratchet 104, which is coupled to the hub 102c via the use of a pin 107, includes a proximal end 104a and a distal end 104b. The distal end 104b includes gears 104c that engage the teeth 103c. When the ratchet 104 is located in a non-activated position, such as shown in FIG. 8, the distal end 102a of the outer member 102 is located in a position relative to the distal end 101a of the inner member 101 and the burr 101c as shown in FIGS. 7 and 8. Activating the ratchet 104, such as shown in FIGS. 10 and 12, moves the outer member 102 axially such that the distal end 102a of the outer member 102 is located in a position relative to the distal end 101a of the inner member 101 and the burr 101c, as shown in FIGS. 9 and 11.

Full distal axial movement of the outer member 102, such that no further movement of the outer member 102 can occur distally towards the burr 101c, is shown in FIGS. 9 and 10, whereas full proximal movement of the outer member 102, such that no further movement of the outer member 102 can occur proximally towards the hub 101d, is shown in FIGS. 11 and 12. It is within the scope of this disclosure that the ratchet 104 may be activated to move the outer member 102 distally to locate the distal end 102a of the outer member 102 relative to the burr 101c between where the distal end 102a is located in FIGS. 11 and 12 and where the distal end is located in FIGS. 9 and 10. Likewise, it is within the scope of this disclosure that the ratchet 104 may be activated to move the outer member 102 proximally to locate the distal end 102a of the outer member 102 relative to the burr 101c between where the distal end 102a is located in FIGS. 9 and 10 and where the distal end 102a is located in FIGS. 11 and 12.

Figure 14A:
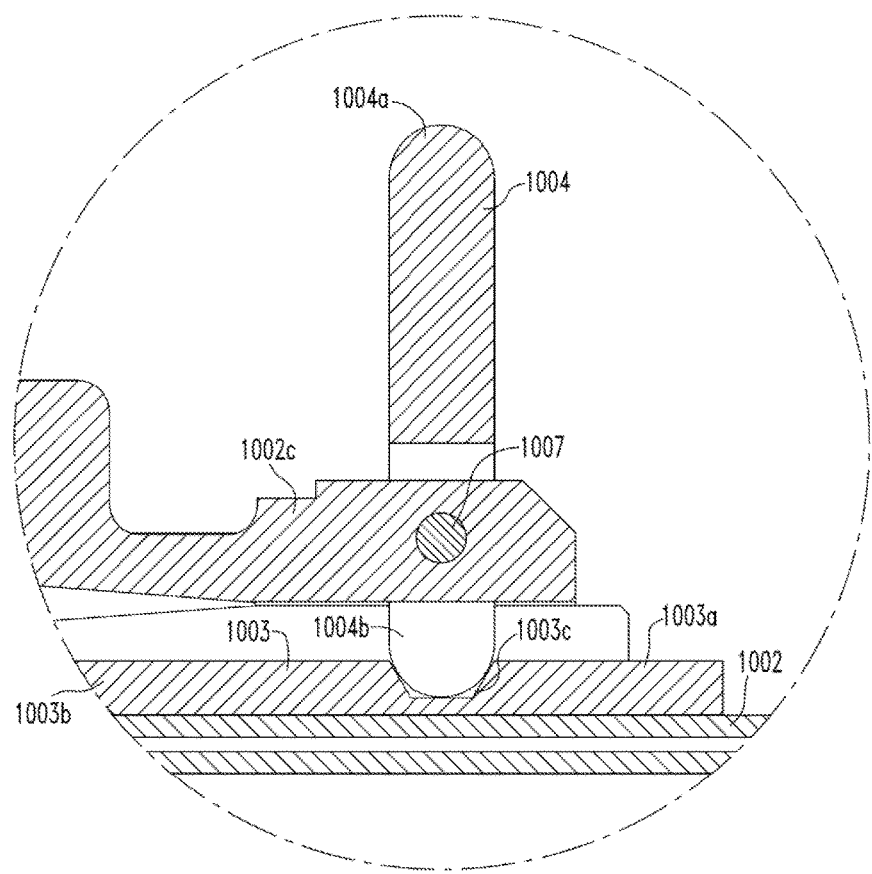
FIG. 14A is an enlarged view of the ratchet as shown in FIG. 14.
Figure 16A:
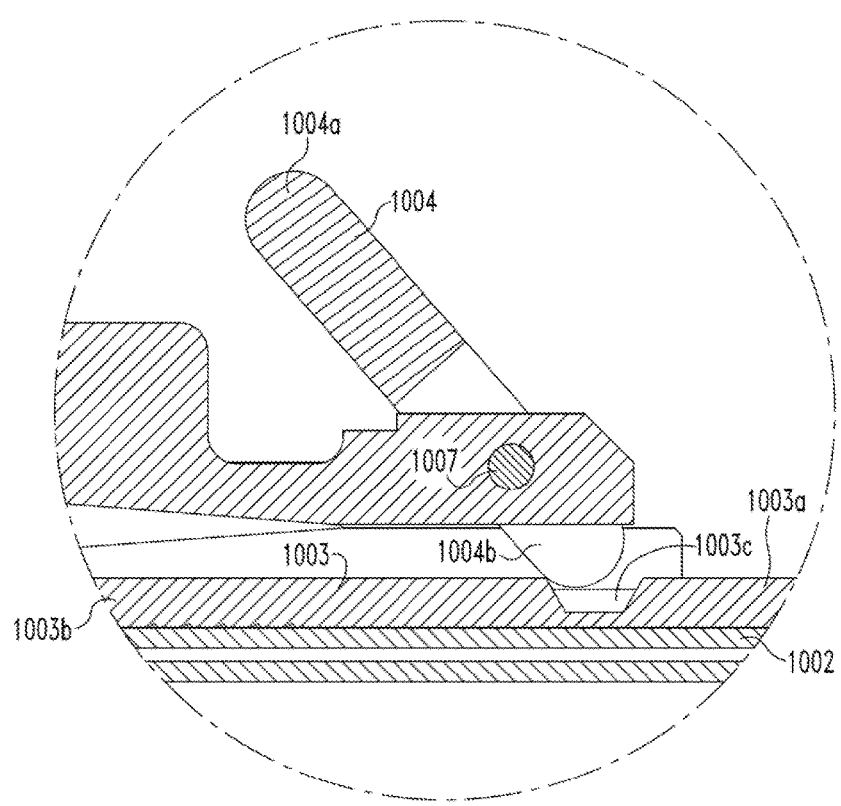
FIG. 16A shows an enlarged view of the lever as shown in FIG. 16.
Figure 18A:
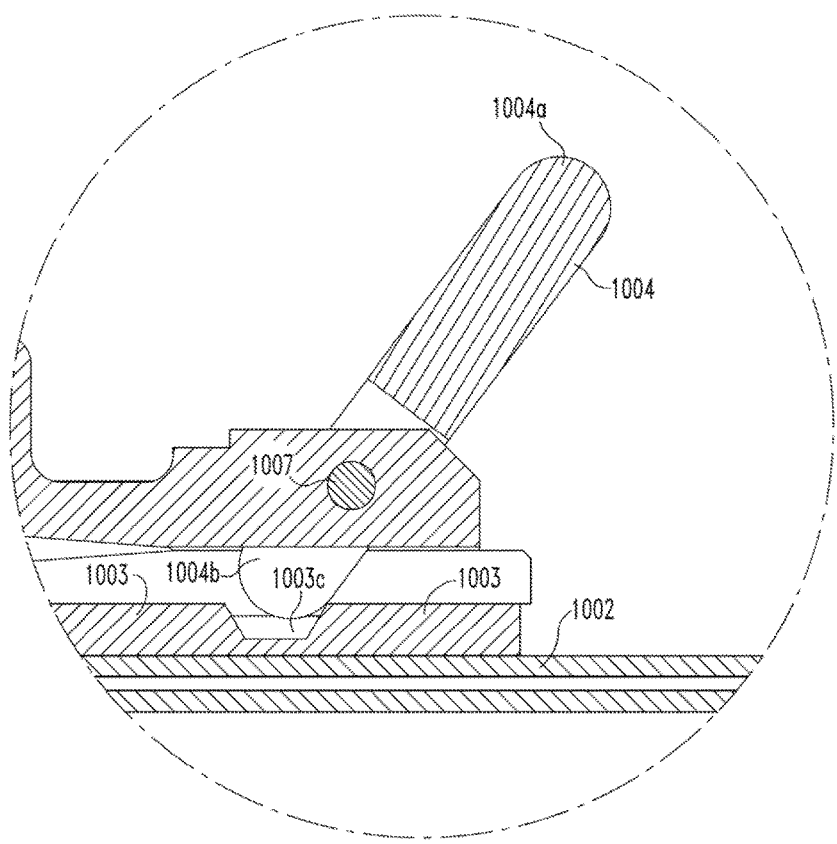
FIG. 18A shows an enlarged view of the ratchet as shown in FIG. 18.

FIGS. 13-18A show the use of a lever 1004 with a tube 1003. Similar to tube 103, tube 1003 includes a distal end 1003a and a proximal end 1003b. The distal end 1003a includes a groove 1003c. The lever 1004, which is coupled to the hub 1002c via the use of a pin 1007, includes a proximal end 1004a and a distal end 1004b. The distal end 1004b engages the groove 1003c. When the lever 1004 is located in a non-activated position, such as shown in FIG. 14, the distal end 1002a of the outer member 1002 is located in a position relative to the distal end 1001a of the inner member 1001 and the burr 1001c as shown in FIGS. 13 and 14. Activating the lever 1004, such as shown in FIGS. 16 and 18, moves the outer member 1002 axially such that the distal end 1002a of the outer member 1002 is located in a position relative to the distal end 1001a of the inner member 1001 and the burr 1001c, as shown in FIGS. 15 and 17.

Full distal axial movement of the outer member 1002, such that no further movement of the outer member 1002 can occur distally towards the burr 1001c, is shown in FIGS. 15 and 16, whereas full proximal movement of the outer member 1002, such that no further movement of the outer member 1002 can occur proximally towards the hub 1001d, is shown in FIGS. 11 and 12. It is within the scope of this disclosure that the lever 1004 may be activated to move the outer member 1002 distally to locate the distal end 1002a of the outer member 1002 relative to the burr 1001c between where the distal end is located in FIGS. 17 and 18 and where the distal end is located in FIGS. 15 and 16. Likewise, it is within the scope of this disclosure that the lever 1004 may be activated to move the outer member 1002 proximally to locate the distal end 1002a of the outer member 1002 relative to the burr 1001c between where the distal end 1002a is located in FIGS. 15 and 16 and where the distal end 1002a is located in FIGS. 17 and 18.

Instead of being located on the outer member 1002, the lever 1004 may be located on a handpiece that the outer member 1002 is connected to and allow for direct or indirect movement of the outer member 1002.

Figure 24A:
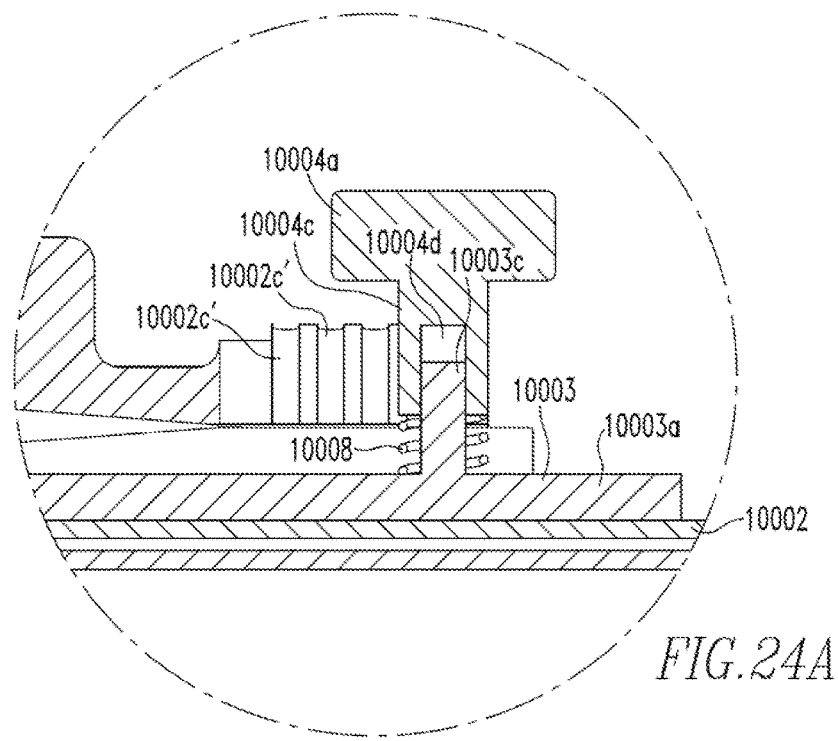
FIG. 24A shows an enlarged view of the slidable button as shown in FIG. 24.
Figure 25:
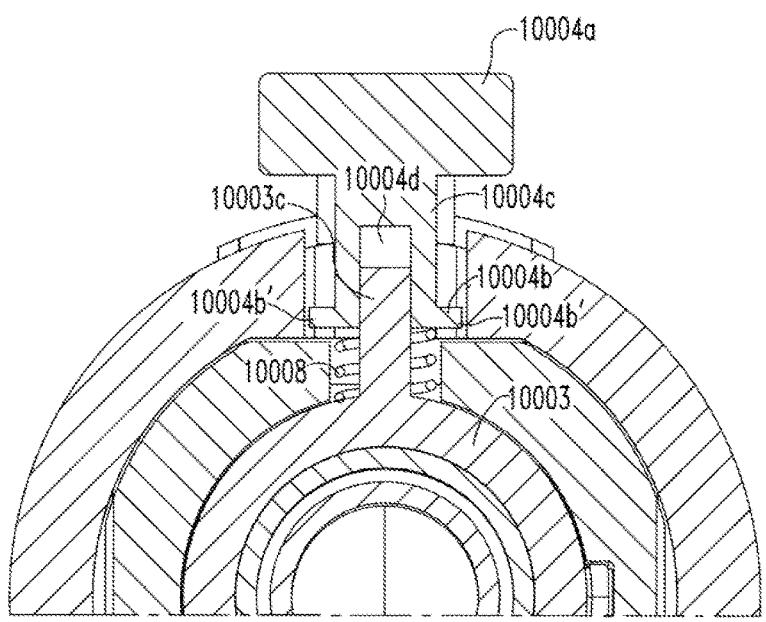
FIG. 25 shows a cross-sectional front view of the slidable button of the arthroscopic resection device of FIG. 19.

FIGS. 19-25 show the use of a slidable button 10004 with a tube 10003. Similar to tubes 103 and 1003, tube 10003 includes a distal end 10003a and a proximal end 10003b. The distal end 10003a includes a tab 10003c housed within an opening 10004d of the button 10004. Disposed around the tab 10003c and located between the button 10004 and the tube 10003 is a spring 10008. As shown in FIG. 25, the button 10004 includes a top portion 10004a, a bottom portion 10004b, and middle portion 10004c. The top portion and bottom portion 10004a, 10004b both have larger diameters than the middle portion 10004c. When the slidable button 10004 is located in a non-activated position, such as shown in FIG. 20, the distal end 10002a of the outer member 10002 is located in a position relative to the distal end 10001a of the inner member 10001 and the burr 10001c as shown in FIGS. 19 and 20. In the non-activated position, the sides 10004b' of the bottom portion 10004b are located within one of the grooves 10002c' of the outer member hub 10002c. Activating the button 10004 requires applying downward pressure on the top portion 10004a so as to depress the button 10004, thereby causing the spring 10008 to compress. The button 10004 is then moved axially along the hub 10002c, thereby causing the outer member 10002 to move axially. Once the distal end 10002a of the outer member 10002 is at the location desired by the user and the bottom portion 10004b is aligned with one of the grooves 10002c', downward pressure on the button 10004 is released by the user and decompression of the spring 10008 causes upward movement of the button 10004 and location of the bottom portion sides 10004b' in the groove 10002c'. Having the bottom portion 10004b' housed within the grooves 10002c' substantially reduces the possibility of inadvertent axial movement of the outer member 10002 by the user.

Figure 20A:
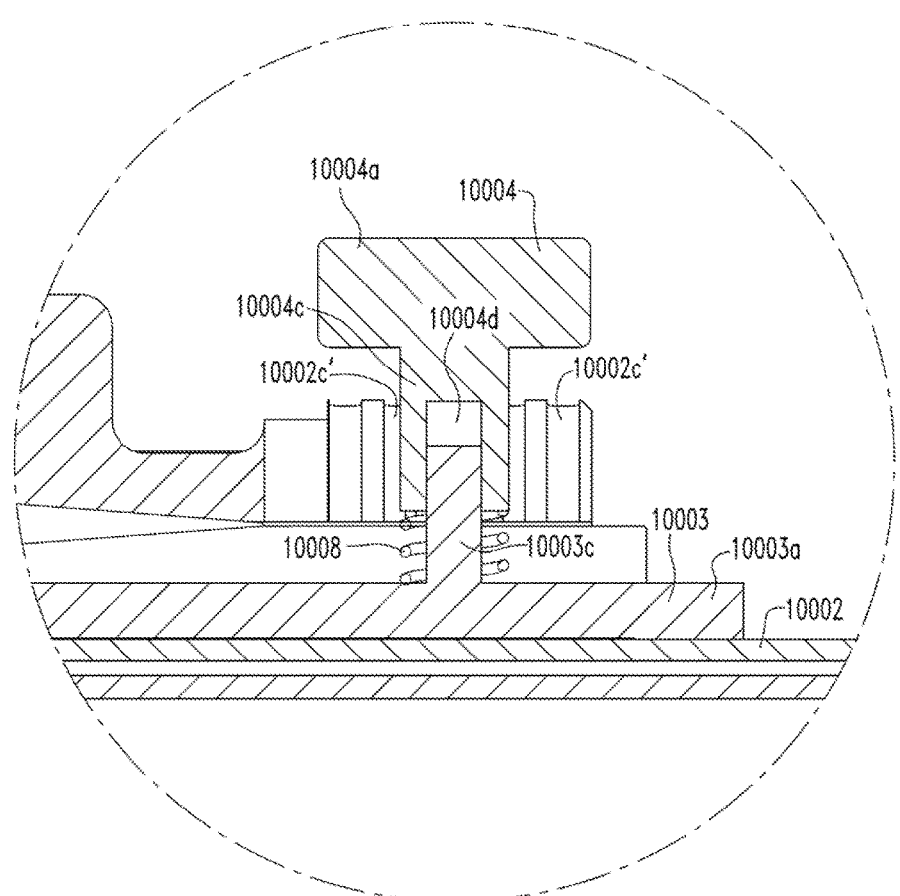
FIG. 20A is an enlarged view of the ratchet as shown in FIG. 20.
Figure 22A:
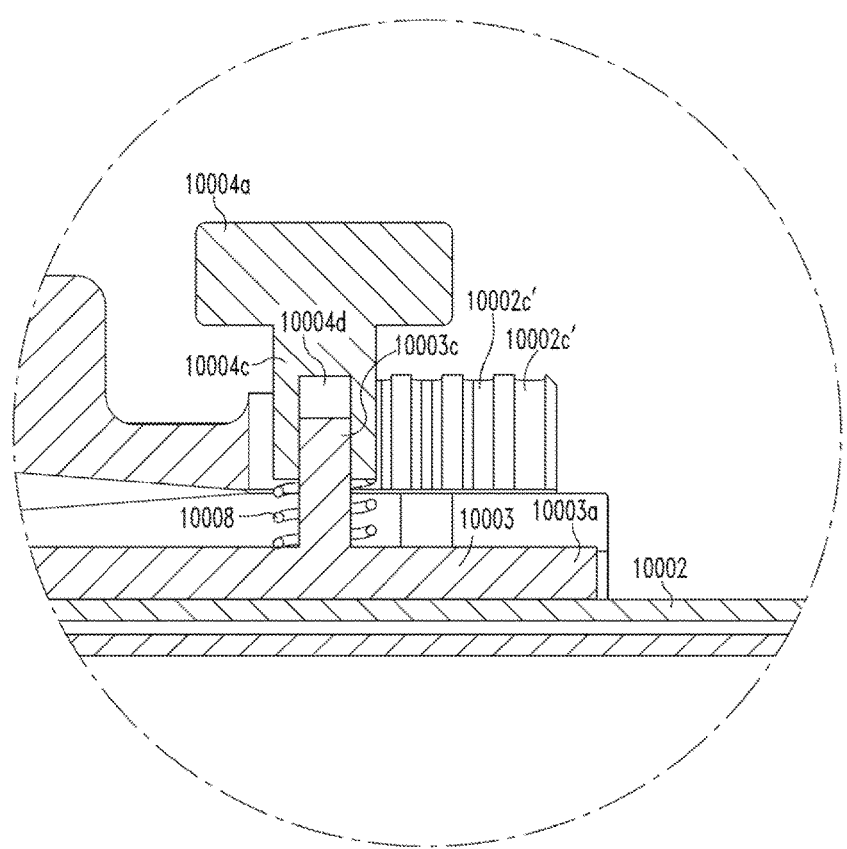
FIG. 22A shows an enlarged view of the slidable button as shown in FIG. 22.

The button 10004 is shown in FIGS. 19-20 and 20A in its non-activated position. In this position, the distal end 10002a of the outer member 10002a is located relative to the burr 10001c, as shown. Full distal axial movement of the outer member 10002, such that no further movement of the outer member 10002 can occur distally towards the burr 10001e, is shown in FIGS. 23 and 24, whereas full proximal movement of the outer member 10002, such that no further movement of the outer member 10002 can occur proximally towards the hub 10001d, is shown in FIGS. 21 and 22. It is within the scope of this disclosure that the button 10004 may be activated to move the outer member 10002 distally to locate the distal end 10002a of the outer member 10002 relative to the burr 1000c between where the distal end 10002a is located in FIGS. 23 and 24 and where the distal end 10002a is located in FIGS. 21 and 22. Likewise, it is within the scope of this disclosure that the button 10004 may be activated to move the outer member 10002 proximally to locate the distal end 10002a of the outer member 10002 relative to the burr 10001c between where the distal end 10002a is located in FIGS. 21 and 22 and where the distal end 10002a is located in FIGS. 23 and 24.

Alternatively, a slidable button, such as slidable button 10004, may be located on the handpiece to allow for longitudinal movement of the outer member 10002. It is also possible for the outer member 12 to have threads on its outer surface that engage threads on a handpiece. The threadable connection between the handpiece and the outer member 12 would allow for longitudinal movement of the outer member 12 via rotation of the outer member 12. Finally, instead of the outer member 12, 102, 1002, 10002 moving longitudinally relative to the inner member 11,101,1001,10001, it is possible for the outer member 12,102,1002,10002 to be fixed and the inner member 11,101,1001,10001 to translate longitudinally relative to the outer member 12, 102, 1002, 10002. This may be done via a connection between the handpiece and the inner member 11,101,1001,10001, as descried above, or by other means known to one of skill in the art.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An arthroscopic resection device comprising:
a cannulated expandable outer member comprising a rigid proximal component and a rigid distal component that is movable relative to the proximal component to lengthen and shorten the cannulated expandable outer member;
an inner member configured to rotatably couple to the proximal component of the cannulated expandable outer member and sized to extend at least partially through the distal component of the cannulated expandable outer member; and
a means for lengthening and shortening the distal component of the cannulated expandable outer member relative to the proximal component and the inner member; and
the inner member is configured to rotate about a long central axis shared by the inner member and the distal component of the cannulated expandable member while the distal component remains stationary relative to the proximal component and the long central axis.

2. The arthroscopic resection device of claim 1 wherein the distal component of the cannulated expandable outer member is a tube.

3. The arthroscopic resection device of claim 1 wherein the proximal component of the cannulated expandable outer member is an outer member hub.

4. The arthroscopic resection device of claim 1 wherein the proximal component of the cannulated expandable outer member is an outer member hub with a cannula and the distal component of the cannulated expandable outer member is a tube and the tube is sized and configured to slide longitudinally in the cannula of the outer member hub.

5. The arthroscopic resection device of claim 1 wherein the inner member includes an inner member hub that is proximal of the cannulated expandable outer member, a shaft coupled to the inner member hub that is housed within the cannula of the cannulated expandable outer member and a cutter coupled to the shaft.

6. The arthroscopic resection device of claim 1 wherein the inner member includes a cutter at a distal end of the inner member that is one of a ball-shaped burr, a flat-ended burr, a helical mill, and a drill.

7. The arthroscopic resection device of claim 1 wherein when the cannulated expandable outer member is in a lengthened state a cutter at a distal end of the inner member does not extend beyond a far distal end of the cannulated expandable outer member.

8. The arthroscopic resection device of claim 1 wherein when the cannulated expandable outer member is in a shortened state a cutter at a distal end of the inner member extends at least in part beyond a far distal end of the cannulated expandable outer member.

9. The arthroscopic resection device of claim 1 wherein the means for lengthening and shortening includes a knob that is rotatably coupled to the proximal component, wherein the knob includes threads, and wherein the distal component includes threads that interact with the threads of the knob such that rotation of the knob relative to the proximal component lengthens the cannulated expandable outer member when the knob is turned in a first direction and shortens the cannulated expandable outer member when the knob is turned in a second direction that is opposite from the first direction.

10. The arthroscopic resection device of claim 9 wherein the means for lengthening and shortening includes a latch mechanism to selectively lock and unlock rotation of the knob relative to the proximal component.

11. An arthroscopic resection device comprising:
a cannulated expandable outer member comprising a rigid proximal component and a rigid distal component that is movable relative to the proximal component to lengthen and shorten the cannulated expandable outer member;
an inner member configured to rotatably couple to the proximal component of the cannulated expandable outer member and sized to extend at least partially through the distal component of the cannulated expandable outer member; and the inner member is configured to rotate about a long central axis shared by the inner member and the distal component of the cannulated expandable member while the distal component remains stationary relative to the proximal component and the long central axis; and a ratchet pivotally coupled to the proximal component, wherein the ratchet includes one or more gear teeth sized and configured to interact with teeth of a rack on the distal component such that pivoting the ratchet relative to the proximal component moves the gear teeth along the teeth of the rack to lengthen the cannulated expandable outer member when the ratchet is pivoted in a first direction and shorten the cannulated expandable outer member when the ratchet is pivoted in a second direction that is opposite from the first direction.

12. An arthroscopic resection device comprising:

a cannulated expandable outer member comprising a rigid proximal component and a rigid distal component that is movable relative to the proximal component to lengthen and shorten the cannulated expandable outer member;

an inner member configured to rotatably couple to the proximal component of the cannulated expandable outer member and sized to extend at least partially through the distal component of the cannulated expandable outer member; and the inner member is configured to rotate about a long central axis shared by the inner member and the distal component of the cannulated expandable member while the distal component remains stationary relative to the proximal component and the long central axis; and a lever pivotally coupled to the proximal component, wherein the lever includes a distal end sized and configured to interact with a groove on the distal component such that pivoting the lever relative to the proximal component pushes against a first side of the groove to lengthen the cannulated expandable outer member when the lever is pivoted in a first direction and pushes against a second side of the groove that is opposite from the first side of the groove to shorten the cannulated expandable outer member when the lever is pivoted in a second direction that is opposite from the first direction.

13. An arthroscopic resection device comprising:

a cannulated expandable outer member comprising a rigid proximal component and a rigid distal component that is movable relative to the proximal component to lengthen and shorten the cannulated expandable outer member;

an inner member configured to rotatably couple to the proximal component of the cannulated expandable outer member and sized to extend at least partially through the distal component of the cannulated expandable outer member; and the inner member is configured to rotate about a long central axis shared by the inner member and the distal component of the cannulated expandable member while the distal component remains stationary relative to the proximal component and the long central axis; and a button coupled to the distal component, the button configured to move between an activated state and a non-activated state by movement of the button perpendicular to the long central axis of the distal component, and in the actuated state the button configured to move along the longitudinal axis relative to the proximal component and simultaneously move the distal component.

14. The arthroscopic resection device of claim 13:

the proximal component further comprises grooves on an upper portion and a wider part closer to the distal component;

the button further comprises bottom portion with sides that extend outward, wherein the button passes through a portion of the proximal component;

the button configured such that in the non-active state the sides interact with the grooves and hold the distal component in fixed relationship to the proximal component relative to the longitudinal axis; and the button further configured such that in the activated state the sides of the bottom portion of the button reside within the wider part of the proximal component, and the button translates along the longitudinal axis which changes the relationship of the distal component relative to the proximal component.

15. The arthroscopic resection device of claim 14 wherein the button is biased away from the distal component so that the bottom portion of the button is biased to contact the grooves of the proximal component.

16. A system for resecting and removing tissue comprising:

an arthroscopic resection device comprising:

a cannulated expandable outer member comprising a rigid proximal component and a rigid distal component that is movable relative to the proximal component to lengthen and shorten the cannulated expandable outer member;

an inner member configured to rotatably couple to the proximal component of the cannulated expandable outer member and sized to extend at least partially through a cannula of the cannulated expandable outer member; and a drive mechanism that is movably coupled to the proximal component and is movably coupled to the distal component of the cannulated expandable outer member such that movement of the drive mechanism relative to the proximal component drives the lengthening or shortening of the cannulated expandable outer member by movement of the distal component relative to the proximal component; and a motor drive coupled to the arthroscopic resection device at the cannulated expandable outer member to secure the motor drive to the arthroscopic resection device and couple at the inner member such that operation of the motor drive turns the inner member while the distal component remains rotationally stationary; and a vacuum source fluidly couple with the arthroscopic resection device to draw cut tissue through and out of the arthroscopic resection device.

17. The system of claim 16 wherein the distal component of the cannulated expandable outer member is a tube.

18. The system of claim 16 wherein the proximal component of the cannulated expandable outer member is an outer member hub.

19. The system of claim 16 wherein the proximal component of the cannulated expandable outer member is an outer member hub with a cannula and the distal component of the cannulated expandable outer member is a tube and the tube is sized and configured to slide longitudinally in the cannula of the outer member hub.

20. The system of claim 16 wherein the inner member includes an inner member hub that is proximal of the cannulated expandable outer member, a shaft coupled to the inner member hub that is housed within the cannula of the cannulated expandable outer member, and a cutter coupled to the shaft.

21. The system of claim 16 wherein the inner member includes a cutter at a distal end of the inner member that is one of a ball-shaped burr, a flat-ended burr, a helical mill, and a drill.

22. The system of claim 16 wherein when the cannulated expandable outer member is in a lengthened state a cutter at a distal end of the inner member does not extend beyond a far distal end of the cannulated expandable outer member.

23. The system of claim 16 wherein when the cannulated expandable outer member is in a shortened state a cutter at a distal end of the inner member extends at least in part beyond a far distal end of the cannulated expandable outer member.

24. The system of claim 16 wherein the inner member includes an opening that extends from a position near its proximal end to a position near its distal end to which the vacuum source may be applied to draw cut tissue through the inner member and out of the arthroscopic resection device.

* * * * *